United States Patent [19]
Wakayama et al.

[11] Patent Number: 6,143,564
[45] Date of Patent: Nov. 7, 2000

[54] USE OF THE POLAR BODY CHROMOSOMES FOR THE PRODUCTION OF EMBRYOS AND NORMAL OFFSPRING

[75] Inventors: Teruhiko Wakayama; Ryuzo Yanagimachi, both of Honolulu, Hi.

[73] Assignee: University of Hawaii, Honolulu, Hi.

[21] Appl. No.: 09/227,365

[22] Filed: Jan. 8, 1999

Related U.S. Application Data

[60] Provisional application No. 60/091,966, Jul. 7, 1998.

[51] Int. Cl.$^7$ ........................... C12N 15/00; C12N 15/02; C12N 15/63; A01K 67/00; A01K 67/027
[52] U.S. Cl. ........................... 435/440; 435/1.1; 435/449; 435/450; 435/455; 800/8; 800/14; 800/21
[58] Field of Search ............................ 800/8, 14, 21; 435/440, 449, 455, 1.1, 450

[56] References Cited

U.S. PATENT DOCUMENTS 4,987,080  1/1991  Grob et al. .............................. 435/325
5,693,534  12/1997  Alak et al. .............................. 435/366

FOREIGN PATENT DOCUMENTS

WO 97/07668  3/1997  WIPO .
WO 98/29532  7/1998  WIPO .

OTHER PUBLICATIONS

Mullins et al J. Clin. Invest. 98(11): S37–S40, see entire document, particularly paragraph bridging pp. 37 and 38, especially p. S38, column 1, lines 23–28, 1996.

Campbell, In Biology, Fourth edition, Benjamin Cummings, publisher, see pp. 653–662, 1995.

Theiler, In The House Mouse, Atlas of Embryonic Development, Springer–Verlag, publishers, pp. 148 and 149, 1989.

Bieber et al Science 213: 775–777, see entire document, especially paragraph bridging columns 2 and 3 on p. 776, Aug. 1981.

Angell, R.R. Polar body analysis: possible pitfalls in pre-implantation diagnosis of chromosomal disorders based on polar body analysis. *Hum. Reprod.* 9: 181–182 (1994).

Campbell, K.H.S. et al. Cell cycle co–ordination in embryo cloning by nuclear transfer. *Review of Reproduction* 2: 40–46 (1996).

Chatot, C.L. et al. Development of 1–cell embryos from different strains of mice in CZB medium. *Biol Reprod.* 42: 432–440 (1990).

Choi, T. et al. The Mos/mitogen–activated protein kinase (MAPK) pathway regulates the size and degeneration of the first polar body in maturing mouse oocytes. *PNAS (USA)* 93: 7032–7035 (1996).

Dyban, A.P. et al. Visualization of second polar body chromosomes in fertilized and artificially activated mouse oocytes treated with Okadaic acid. *J. Assist. Reprod. Gene.* 9: 572–579 (1992).

Edwards, R.G. & Gates, A.H. Timing and the stages of maturation divisions, ovulation, fertilization and first cleavage of eggs of adult mice treated with gonadotropins. *J. Endocrinol.* 18: 292–304 (1959).

Egozcue, J. Polar body analysis: possible pitfalls in preconception diagnosis of single gene and chromosome disorder. *Hum. Reprod.* 5: 826–829 (1994).

Evsikov, A.V. & S.V. A Evsikov, study of the first and second polar bodies in mouse oogenesis. *Russ. J. Dev. Biol.* 26: 196–200 (1995).

Feng, J.L. & Ha.., J.L. Birth of normal mice after electrofusion of the second polar body with the male pronucleus: a possible treatment for oocyte–factor infertility. Am. Soc. Reprod. Med. Annual Meeting 1997: Abstract P–050.

Hogan, B. et al. Manipulating the mouse embryo: Laboratory Manual Section D. Cold Spring Harbor: Cold Spring Harbor Laboratory: 191 (1986).

Kimura, Y. & Yanagimachi, R. Intracytoplasmic sperm injection in the mouse. *Biol. Reprod.* 52:709–720 (1995).

Kimura, Y. & Yanagimachi, R. Mouse oocytes injected with testicular spermatozoa or round spermatids can develop into normal offspring. *Development* 121: 2397–2405 (1995).

Kono, T. et al. Thymocyte transfer to enucleated oocytes in the mouse. *J. Reprod. Dev.* 39: 301–307 (1993).

Kuretake. S. et al. Fertilization and development of mouse oocytes injected with isolated sperm heads. *Biol. Reprod.* 55: 789–795 (1996).

Masui, Y & Clarke, H.J. Oocyte maturation. *International Review of Cytology*, 57: 185–282 (1979).

Munne, S. et al. The use of the first polar bodies for preimplantation diagnosis of aneuploidy. *Mol. Hum. Reprod.* 10: 1014–1020 (1995).

Ortiz, M.E. et al. Postovulatory aging of human ova: II. Spontaneous division of the first polar body. *Gamete Research* 7: 269–276 (1983).

Rodman, T.C. Chromosomes of the first polar body in mammalian meiosis. *Exp. Cell Res.* 68: 205–210 (1971).

Takase, K. et al. Apoptosis in the degenerated process of unfertilized mouse ova. *Tohuku J. Exp. Med.* 175: 69–76 (1995).

(List continued on next page.)

*Primary Examiner*—Bruce R. Campell
*Assistant Examiner*—Richard Schnizer
*Attorney, Agent, or Firm*—Jones, Day, Reavis & Pogue

[57] ABSTRACT

The invention provides a method for obtaining a live offspring having maternal chromosomes derived from a live first polar body of an oocyte that has completed the first meiotic division. It has been discovered herein that chromosomes in the first polar body are able to participate in normal embryonic development if they are allowed to complete the second meiotic division within an enucleated mature oocyte, and are then allowed to mingle with chromosomes of a spermatozoon. The invention further provides a method for producing up to four embryos or live offspring having the chromosomes of a single oocyte, by using both the first polar body chromosomes, and the second polar body chromosomes to reconstitute recipient enucleated (fertilized) oocytes.

15 Claims, 5 Drawing Sheets

OTHER PUBLICATIONS

Verlinsky, Y. et al. Analysis of the first polar body: preconception genetic diagnosis. *Hum. Reprod.* 10: 1014–1020 (1990).

Verlinsky. Y. et al. Polar body diagnosis of common aneuploids by FISH. *J. Assist. Reprod. Gene.* 13: 157–162 (1996).

Wakayama, T., Hayashi, Y. & Agura, A. Participation of the female pronucleus derived from the second polar body in full embryonic development of mice. *J. Reprod. Fertil.* 110: 263–266 (1997).

Wheeler, M.B. et al. Production of live offspring with predicted genotypes using PCR–RFLP analysis of polar bodies from mouse oocytes. *Mol. Reprod. Dev.* 40: 267–272 (1995).

Yanagida, K. & Yanagimachi, R. et al. Thermostability of sperm nuclei assessed by microinjection into hamster oocytes. *Biol Reprod.* 44: 440–447 (1991).

Durban, M. et al. Chromosome studies in first polar bodies from hamster and human oocytes. *Hum.Reprod.* 13: 583–587 (1998).

Ogura, A. et al. Development of normal mice from metaphase I oocytes fertilized with primary spermatocytes. Proc. Natl. Acad. Sci. USA 95: 5611–5615 (1998).

Wakayama, T. & Yanagimachi, R. The first polar body can be used for the production of normal offspring in mice. *Biol. Reprod.* 59: 100–104 (1998).

USE OF THE POLAR BODY CHROMOSOMES FOR THE PRODUCTION OF EMBRYOS AND NORMAL OFFSPRING

This application claims the benefit of U.S. Provisional Patent Application, Ser. No. 60/091,966, filed Jul. 7, 1998.

The U.S. Government has a paid-up license in this invention and the right in limited circumstances to require the patent owner to license others on reasonable terms as provided for by the terms of contract numbers R01-HD-03402 and R01-HD-34362 awarded by The National Institute of Child Health and Human Development, the National Institutes of Health, Public Health Services.

BACKGROUND OF THE INVENTION

The invention relates to the development of embryos and normal offspring from fertilized enucleated recipient oocytes that have been reconstituted with polar body chromosomes. The invention further relates to the development of multiple embryos and multiple live offspring having the genetic material from a single oocyte.

The meiotic division of mammalian oocytes differs in several significant ways from that of male germ cells. In the male, as a result of meiotic divisions of single diploid cells (spermatogonia), sets of four haploid round spermatids with an equal volume of cytoplasm are formed. Each of these spermatids then develops into a spermatozoon. However, in the female, one primary germ cell (oocyte) gives rise to only one mature ovum (egg). During meiotic division of the oocyte, two small polar bodies (the first and second polar bodies), each containing a set of chromosomes and very little cytoplasm, are sequentially extruded from the large main egg body. Neither of these polar bodies serves any known function. Rather, they each degenerate sometime during the pre-implantation period and do not participate in embryonic development. Each of the polar bodies has been used for pre-implantation diagnosis of gene defects and chromosomal disorders in humans, as an alternative to embryonic biopsy diagnosis.

In normal mammalian development, oocytes become developmentally arrested in the ovaries at the germinal vesicle stage in prophase of the first meiotic division. Upon appropriate stimulation (e.g., a surge in plasma luteinizing hormone), meiosis resumes, the germinal vesicle breaks down, and the first meiotic division is completed with the extrusion of a diploid set of chromosomes into the first polar body, another diploid set of chromosomes remaining within the cytoplasm of the oocyte. The oocyte then becomes arrested at metaphase of the second meiosis ("Met II"). Met II oocytes (mature oocytes) can then be ovulated and fertilized. Once fertilized, the oocyte completes the second meiotic division with the extrusion of a haploid set of chromosomes into the second polar body, male and female pronuclei are formed, and DNA replication is initiated in the pronuclei. The male and female pronuclei then fuse together, allowing their chromosomes to mingle. Equal segregation of the genetic material occurs by mitosis and the zygote cleaves to form two daughter blastomeres. The embryos continue to develop by undergoing a series of mitotic divisions before differentiating into specific cells, resulting in the organization of tissues and organs. This developmental program ensures the successful transition from oocyte to offspring.

Recently, it has been demonstrated in the mouse that the female pronucleus can be removed from a fertilized oocyte and replaced with the second polar body chromosomes from the same or a different oocyte and, providing they are synchronized in age with the male pronuclei, the second polar body chromosomes are competent to support embryonic development resulting in live mouse offspring. The first polar body has been shown to be extremely unstable. For example, in mouse oocytes, more than half of the first polar bodies degenerate within a few hours after ovulation, and the vast majority disintegrate during the next 12 hours. In contrast, in humans it has been demonstrated that many first polar bodies persist for more than 20 hours after ovulation. In general, it is believed that the first polar body in eutherian (placental) mammals has a shorter life than the second polar body. Although degeneration of polar bodies (and of unfertilized oocytes as well) is likely to be an apoptotic process, the factors that determine the individual and species differences in the degeneration rates of polar bodies (and of unfertilized oocytes) are not understood.

It has never been determined whether the chromosomes within the first polar body have the same genetic and reproductive potential as those left within the secondary oocyte after the first meiotic division. That is, it has never been determined whether the chromosomes of the first polar body can participate in normal embryonic development and support the production of live offspring. An advantage to be gained by utilizing the first polar body chromosomes to obtain a live offspring, in addition to a live offspring produced from the normal fertilized ovum, is that two offspring could be obtained that have chromosomes (i.e. the genetic information) obtained from a single oocyte. Moreover, if second polar body chromosomes from both the normal fertilized ovum and the fertilized first polar body chromosome recipient oocyte were similarly utilized to obtain live offspring, it is theoretically possible to produce four individual offspring using the chromosomes from a single donor oocyte, providing that oocytes suitable as recipients of the chromosomes are available.

The advantages of such a method could be enormous. For example, multiple offspring could be produced that contain the genetic information from a single oocyte of a female whose genetic information it would be desirable to propagate (e.g., a zoo animal, an endangered mammalian species, a non-human primate, a human, or an animal having superior breeding, such as a race horse, livestock, and the like). Moreover, since each recipient oocyte would be fertilized by a different spermatozoon and, because the genotypes of the polar bodies may not be identical to each other or to the donor oocyte, these offspring would not be clones, thus providing the opportunity to increase the genetic diversity of the offspring.

SUMMARY OF THE INVENTION

The invention provides a method for obtaining a live offspring having chromosomes derived from a live first polar body of an oocyte that has completed the first meiotic division. It has been discovered herein that live first polar body chromosomes are capable of undergoing the second meiosis after transfer into mature oocytes, regardless of the postovulatory age of the chromosomes. Thus, chromosomes within live first polar bodies that are destined to degenerate can be rescued by being transferred into the mature ooplasm. Moreover, it has been discovered herein that chromosomes within the first polar body have the same genetic and reproductive potential as those left in the oocyte after the first meiotic division. In particular, it has been discovered that chromosomes in the first polar body are able to participate in normal embryonic development if they are allowed to complete the second meiotic division within an enucleated mature oocyte, and are then allowed to mingle with chromosomes of a spermatozoon.

By the method according to the invention, a live first polar body is harvested from an oocyte and at least a portion of the first polar body that includes all of the chromosomes is introduced into a recipient oocyte from which the resident chromosomes have been removed (i.e., an enucleated oocyte), to form a chromosomally reconstituted recipient oocyte. The recipient oocyte may be from the same animal or from another animal of the same or a related species. As used herein, the term "introduced" is intended to encompass any method by which the first (and/or the second) polar body chromosomes may enter the enucleated oocyte, including microinjection or the fusing of the polar body(ies) and the oocyte as mediated by fusion-promoting chemicals, by electricity or by a fusogenic virus, and the like, as known to those skilled in the art. Within the recipient oocyte, the first polar body chromosomes are transformed into Met II chromosomes. The recipient oocyte is then fertilized by a live spermatozoon or by insertion of at least a sperm nucleus into the oocyte. Embryonic development may then be facilitated to allow the resulting embryo to develop into a live offspring. The resulting embryo/offspring has the maternal chromosomes from the first polar body.

The invention further provides a method for producing multiple embryos or live offspring having the chromosomes of a single oocyte. This method takes advantage of the use of both the first polar body chromosomes and the second polar body chromosomes to transmit the genetic information from a single oocyte to up to four embryos/offspring. According to this method, a live first polar body is harvested from a first oocyte, and the first polar body chromosomes are introduced into a recipient enucleated oocyte which is then fertilized, resulting in the production of one embryo, as described above. The first oocyte, from which the first polar body has been harvested, has retained its original chromosomes and is fertilized, resulting in the production of a second embryo. During the second meiotic division after fertilization, this first oocyte produces a second polar body, which may be harvested and its chromosomes introduced into another fertilized recipient enucleated oocyte, which is allowed to develop into a third embryo. Meanwhile, the fertilized recipient of the first polar body chromosomes produces a second polar body upon completion of the second meiotic division. The method may thus further include the step of introducing chromosomes from this second polar body into yet another fertilized recipient enucleated oocyte, which is allowed to develop into a fourth embryo. Any of the first, second, third or fourth embryos may then be transferred to surrogate mothers and allowed to develop into live offspring.

The invention further provides embryos and live mammals, such as primates (including humans), sheep, cattle, pigs, bears, cats, dogs, horses, rodents, and the like, produced by the process of the invention. It has been discovered herein that live mammals produced by the process of the invention are themselves capable of reproduction.

Fertilization of the recipient oocyte(s) may take place by exposing the oocyte to a live spermatozoon either in vivo or in vitro, depending on whether the transferred chromosomes are from the first or the second polar bodies, as discussed further below. Alternatively, fertilization of the recipient oocyte may take place in vitro by insertion of a whole spermatozoon or the head (or demembranated head) of a spermatozoon directly into the oocyte by microinjection, preferably piezo electrically-actuated microinjection. The spermatozoon head may be from a fresh spermatozoon, a frozen/thawed spermatozoon, or a reconstituted freeze-dried spermatozoon. A method for preserving spermatozoon by freeze-drying is disclosed in our copending U.S. patent application, Ser. No. 09/177,391, filed Oct. 23, 1998, the disclosure of which is hereby incorporated by reference.

Prior to, during, or after any of the steps of introducing polar body chromosomes into the enucleated recipient oocytes, or fertilization of the oocytes, the method may further include the step of introducing a reagent, such as a modulator of embryonic development, into the oocytes. For example, the reagent may comprise an exogenous protein, a derivative of an exogenous protein, an antibody, a pharmacological agent, and the like, or combinations of these. Furthermore, an exogenous nucleic acid or a derivative of an exogenous nucleic acid may similarly be introduced into the recipient oocyte(s) to produce transgenic embryos.

DETAILED DESCRIPTION OF THE INVENTION

The invention provides a method for obtaining a live offspring from an enucleated recipient oocyte reconstituted with the chromosomes of a first polar body from the same oocyte or from another (donor) oocyte. By the method of the invention, fertilization of the chromosomally reconstituted enucleated oocyte results in the formation of an embryo that comprises first polar body chromosomes rather than the chromosomes of the mature egg. Thus, in one embodiment, the steps of the method of the invention include: (i) collecting a live first polar body from a first oocyte; (ii) introducing at least a portion of the first polar body that includes all of the chromosomes into an enucleated recipient oocyte to form a chromosomally reconstituted recipient oocyte; (iii) fertilizing the reconstituted recipient oocyte; and (iv) allowing the fertilized reconstituted recipient oocyte to develop into an embryo. The method may further include the step of allowing the embryo to develop into a live offspring, such as by transferring the embryo to a female surrogate recipient, wherein the embryo develops into a viable fetus.

In another embodiment, the invention provides a method for producing at least two embryos using the chromosomes of a single oocyte, comprising the steps of: (i) collecting a live first polar body from a first oocyte; (ii) fertilizing the first oocyte after removal of the first polar body; (iii) allowing the first fertilized oocyte to develop into a first embryo; (iv) introducing at least a portion of the live first polar body that contains the chromosomes into an enucleated second oocyte to form a chromosomally reconstituted second oocyte; (v) fertilizing the reconstituted second oocyte; and (vi) allowing the fertilized reconstituted second oocyte to develop into a second embryo.

To obtain a third embryo using the chromosomes of the first oocyte, the method further includes the steps of: (vii) harvesting a live second polar body from the fertilized first oocyte; (viii) obtaining a fertilized enucleated third oocyte; (ix) introducing at least a portion of the live second polar body that contains the chromosomes into the fertilized enucleated third oocyte; and (x) allowing the fertilized third oocyte to develop into a third embryo.

To obtain a fourth embryo using the chromosomes of the first oocyte, the method further includes the steps of: (xi) obtaining a live second polar body from the fertilized second oocyte; (xii) obtaining a fertilized fourth enucleated oocyte; (xiii) introducing at least a portion of the second polar body from the fertilized second oocyte into the fertilized enucleated fourth oocyte, wherein the introduced portion of the second polar body contains the chromosomes; and (xiv) allowing the fertilized fourth oocyte to develop into a fourth embryo.

Figure 5:
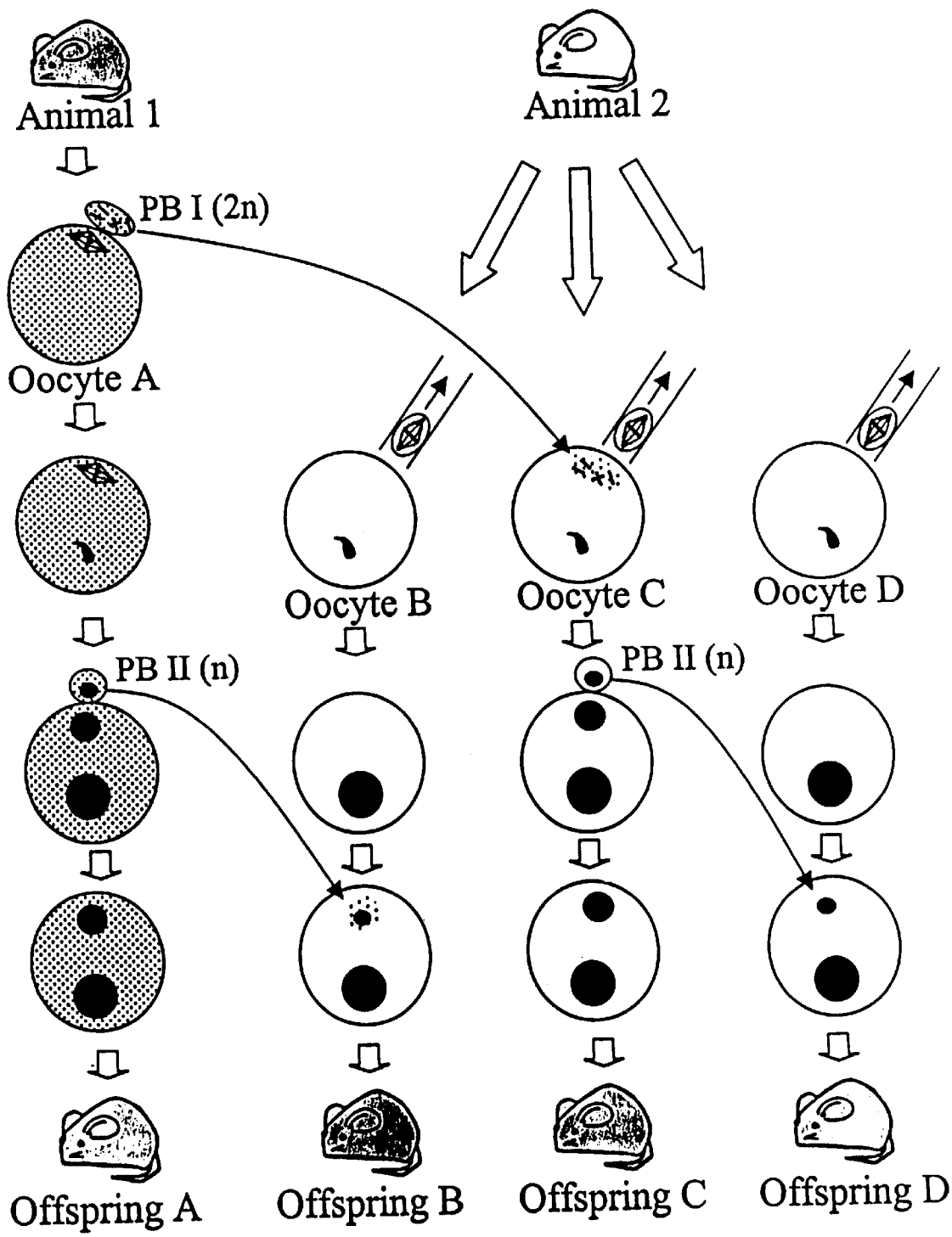
FIG. 5 is a diagrammatic representation of the invention method for producing four offspring using the chromosomes of a single oocyte.

One embodiment of the methods of the invention is schematically illustrated in FIG. 5. The first polar body (PB 1) is harvested from oocyte A from animal 1, and is transferred into an enucleated oocyte C from animal 2. The numbers "2n" or "n" refer to ploidy of the chromosomes, rather than the centromere number per se. Oocyte A is then fertilized/activated by injection of a single sperm head, forms two pronuclei and a second polar body (PB II), and eventually develops into offspring A.

In oocyte C, after the first polar body chromosomes transform into metaphase II chromosomes, a single sperm head is injected. Thus, oocyte C is fertilized/activated, forms two pronuclei and the second polar body (PB II), and eventually develops into offspring C.

Meanwhile, oocyte D (which is also from animal 2) is enucleated and injected with a single sperm head. After the sperm head transforms into a pronucleus in the fertilized/activated oocyte D, a harvested second polar body from oocyte C is injected. This oocyte D then develops into offspring D. Offspring B is similarly produced by transferring the second polar body harvested from oocyte A into enucleated fertilized oocyte B (which is also from animal 2).

Embodiments of the individual steps and substeps of the methods of the invention are now presented in greater detail.

The Recipient Oocytes

Recipient oocytes that may be used in the method of the invention include both immature (e.g., GV stage) that are subsequently matured in vitro, and mature (i.e., Met II stage) oocytes that have been harvested from an animal. Mature oocytes may be obtained, for example, by inducing an animal to superovulate by injections of gonadotrophic or other hormones (for example, sequential administration of equine and human chorionic gonadotrophin) and surgical harvesting of ova shortly after ovulation (e.g., 80–84 hours after the onset of estrous in the domestic cat, 72–96 hours after the onset of estrous in the cow and 13–15 hours after the onset of estrous in the mouse). Where it is only possible to obtain immature oocytes, they are cultured in a maturation-promoting medium until they have progressed to Met II; this is known as in vitro maturation ("IVM"). Methods for IVM of immature bovine oocytes are described in WO 98/07841, and for immature mouse oocytes in Eppig & Telfer (*Methods in Enzymology* 225, 77–84, Academic Press, 1993).

The stage of in vivo maturation of the oocyte at enucleation and cellular nuclear reconstitution has been previously reported to be significant to the success of in vitro nuclear transfer methods for producing embryos. It is known that the chemistry of the oocyte cytoplasm changes throughout the maturation process. For example, a cytoplasmic activity associated with maturation, metaphase-promoting factor ("MPF"), is high in immature oocytes at metaphase of the first meiotic division, declining with the formation and expulsion of the first polar body, and again reaching high levels at Met II. MPF activity remains high in oocytes arrested at Met II, rapidly diminishing upon oocyte activation. In general, reports of mammalian nuclear transfer describe the use of Met II oocytes as recipients. Met II oocytes are of the type ready to be activated by fertilizing spermatozoa. When a cell nucleus is introduced into the cytoplasm of an enucleated Met II oocyte (i.e., one with high MPF activity), its nuclear envelope (if it has one) breaks down and chromatin condenses, resulting in the formation of metaphase chromosomes.

Recipient oocytes are surgically harvested from oviducts as oocyte-cumulus cell complexes and placed in a buffered medium, such as Hepes-CZB medium (described below). Cumulus cells are dispersed with a dispersing enzyme, such as 0.1% bovine testicular hyaluronidase (e.g., 300 USP units/mg, ICN Pharmaceuticals, Costa Mesa, Calif.). It is preferred that cumulus-free oocytes are kept in a medium, such as CZB medium, at 37.5° C. under 5% $CO_2$ in air, under mineral oil (such as that available from E. R. Squibb and Sons, Princeton, N.J.) for less than one hour before further treatments.

Oocyte Enucleation

Preferably, the Met II oocyte is exposed to a medium containing a microfilament disrupting agent or tubulin-disrupting agent prior to and during enucleation. Disruption of the microfilaments imparts relative fluidity to the cell membrane and underlying cortical cytoplasm, such that a portion of the oocyte enclosed within a membrane can easily be aspirated into a pipette with minimal damage to cellular structures. One microfilament-disrupting agent of choice is cytochalasin B (5 µg/mL). Other microfilament-disrupting agents are also known and include, but are not limited to, cytochalasin D. Suitable microtubule-disrupting agents, such as nocodazole, vinblastin and colchicine, are known to those skilled in the art.

In one preferred embodiment of the invention, the enucleation of the Met II oocyte is achieved by aspiration using a piezo electrically-actuated micropipette. The Met II oocyte is suspended in the medium under mineral oil, as known to those skilled in the art. Throughout the enucleation microsurgery, the Met II oocyte is anchored by a conventional holding pipette and the flat tip of a piezo electrically-driven enucleation pipette (internal diameter≈10 μm) is brought into contact with the zona pellucida. A suitable piezo electric driving unit is sold under the name of Piezo Micromanipulator/Piezo Impact Drive Unit by Prime Tech Ltd. (Tsukuba, Ibaraki-ken, Japan). The unit utilizes the piezo electric effect to advance, in a highly controlled, rapid manner, the (injection) pipette holder a very short distance (approximately 0.1 μm). The intensity and interval between each pulse can be varied and are regulated by a control unit.

Piezo pulses (for example, intensity=1–5, speed=4–16) are applied to advance (or drill) the pipette through the zona pellucida while maintaining a small negative pressure within the pipette. In this way, the tip of the pipette rapidly passes through the zona pellucida and is thus advanced to a position adjacent to the Met II plate (discernible as a translucent region in the cytoplasm of the Met II oocytes of several species, often lying near the first polar body). Oocyte cytoplasm containing the metaphase plate (which contains the chromosome-spindle complex) is then gently and briskly sucked into the injection pipette without breaking the plasma membrane and is gently pulled away from the oocyte until a stretched cytoplasmic bridge is pinched off. The effect of this procedure is to remove that part of the oocyte cytoplasm containing all of the Met II chromosomes.

Where appropriate, batches of oocytes may be screened to confirm complete enucleation. For oocytes with granular cytoplasm (such as porcine, ovine and feline oocytes), staining with a DNA-specific fluorochrome (e.g., Hoeschst 33342) and brief examination with low UV illumination (enhanced by an image intensified video monitor) is advantageous in determining the efficiency of enucleation.

Enucleation of the Met II oocyte may be achieved by other methods, such as that described in U.S. Pat. No. 4,994,384. For example, enucleation may be accomplished microsurgically using a conventional micropipette, as opposed to a piezo electrically-driven micropipette. This can be achieved by slitting the zona pellucida of the oocyte with a glass needle along 10–20% of its circumference close to the position of the Met II chromosomes (the spindle is located in the cortex of the oocyte by differential interference microscopy). The oocyte is placed in a small drop of medium containing cytochalasin B in a micromanipulation chamber. Chromosomes are removed with an enucleation pipette having a sharpened, beveled tip.

After enucleation, the oocytes are ready to be reconstituted with the first polar body chromosomes, or to be fertilized prior to being reconstituted with the second polar body chromosomes. It is preferred to prepare enucleated oocytes within about 2 hours before reconstitution.

Preparation of Polar Bodies (A) First Polar Body.

Oviductal oocytes containing first polar bodies may be obtained by inducing an animal to ovulate by injections of gonadotrophic or other hormones and surgical harvesting of oocytes shortly after ovulation, as described above. The viability of polar bodies within the perivitelline space of isolated oviduct oocytes can be assessed by using a cell viability test, such as the commercially available kit, "Live/dead FertiLight" from Molecular Probes, Inc., Eugene, Oreg., that differentiates between plasma membrane-intact ("live") and damaged ("dead") cells according to the fluorescence staining pattern under a UV microscope. The chromosomes in live polar bodies with intact plasma membranes fluoresce green, whereas those in dead polar bodies fluoresce bright orange-red.

Figure 1:
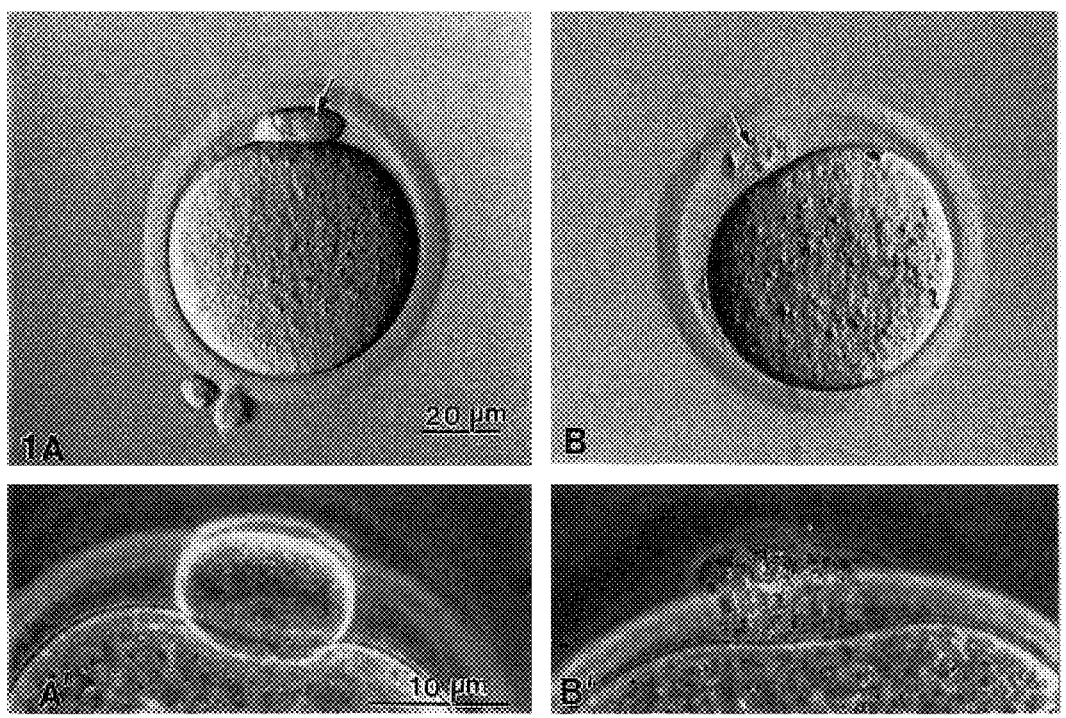
FIGS. 1A–1B' illustrates photomicrographs of live (A and A') and dead (B and B') first polar bodies (arrows) seen with interference-contrast optics and phase-contrast optics, respectively. Live polar bodies with intact plasma membranes have relatively clear cytoplasm, whereas dead polar bodies, with broken or missing plasma membranes, have granular cytoplasm.

It has been observed that, in the mouse, polar bodies that are "live" have a sharply defined, smooth membrane and clear cytoplasm, as illustrated in FIG. 1A. The chromosomes in the live polar bodies are scattered, stretched, or adherent to each other. It has also been observed that some "dead" polar bodies have a smooth plasma membrane, but in most the membrane is rough or missing. The most easily recognizable feature of the dead polar body is a very granulated cytoplasm, regardless of the state of the plasma membranes and chromosomes, as illustrated in FIG. 1B. It has been found herein that dead polar bodies do not transform into typical metaphase chromosomes (see FIG. 3D) in the method of the invention and, therefore, do not support embryonic development. Consequently only oocytes with live first polar bodies are selected for microsurgical harvesting of the polar body for injection into an enucleated recipient oocyte.

Harvesting of the first polar body chromosomes is preferably performed by a technique that is similar to that already described for oocyte enucleation. For example, an oocyte with a live first polar body is selected and its zona pellucida penetrated with an injection pipette, either manually or with a piezo electrically-actuated injection pipette. The entire first polar body is then gently sucked into the injection pipette. Alternatively, the first polar body may be obtained by removing the zona pellucida mechanically or by dissolving the zone enzymatically or chemically (e.g., with zona-dissolving enzymes, such as pronase or an acidic medium such as a modified Tyrode solution with a pH of 2.5. Acidic Tyrode solution is known to those skilled in the art and may be prepared according to the method in "Manipulating the Mouse Embryo". A Laboratory Manual, Second Edition, Cold Spring Harbor Laboratory press, 1994).

The plasma membrane of the polar body is broken by sucking the polar body in and out of the pipette, and the contents of the polar body (including all the chromosomes) are immediately injected into an enucleated oocyte, as described further below. Alternatively, polar body chromosomes may be incorporated into oocyte cytoplasm by electrofusion of the polar body with the oocyte. Other methods of fusion are well known to those skilled in the art, including the use of DNA-inactivated Sendai virus or fusion-promoting chemicals.

(B) Second Polar Body.

Second polar bodies may be obtained, for example, from the pronucleus stage of fertilized oocytes of animals that have been ovulated spontaneously or induced to ovulate and have been mated with males around the time of ovulation. Fertilized oocytes may be obtained surgically from oviducts within 6 to 24 hours after ovulation and freed from cumulus cells by treatment with a dispersing enzyme, such as hyaluronidase, as described above. The second polar body is identified on the basis of its inclusion of a round nucleus. In contrast, the first polar body contains scattered chromosomes.

Alternatively, second polar body may be obtained from oocytes that have undergone parthenogenetic activation. For example, Met II oocytes may be activated in vitro to undergo the second meiotic division, accompanied by the formation of the second polar body. Oocyte activation may be achieved by various means known to those skilled in the art including, but not limited to, electroactivation, or exposure to ethyl alcohol, sperm cytoplasmic factors, oocyte receptor ligand peptide mimetics, pharmacological stimulators of $Ca^{2+}$ release (e.g., caffeine), $Ca^{2+}$ ionophores (e.g., A2318, ionomycin), strontium ions ($Sr^{2+}$), modulators of phosphoprotein signaling, inhibitors of protein synthesis, and the like, or combinations thereof.

Regardless of the method of activation of the oocyte, the second polar body may be removed as described above for the first polar body.

Introduction of First Polar Body Chromosomes Into Enucleated Oocytes

When first polar bodies are prepared as described above, they may be introduced into the enucleated oocytes by microinjection or by membrane fusion techniques, such as those described above (e.g., electricity, fusion-promoting chemicals, a fusogenic virus, and the like).

For example, in a technique for membrane fusion by electricity, an enucleated oocyte is held in a small drop of a medium such as CZB. A first polar body having an intact plasma membrane is inserted by means of a micropipette through the zona pellucida into the perivitelline space of the recipient oocyte. The oocyte/first polar body pair is then placed in a drop (10 μL) of a fusion medium (300 millimoles per liter (mmol/L) of mannitol, 0.05 mmol/L $CaCl_2$, 0.1 mmol/L $MgSO_4$, and 5 mg/mL polyvinylpyrrolidone.) between the electrodes of a circular electrofusion chamber (such as that available from Shimadzu, Kyoto, Japan). The width and depth of the electrode gap are 0.5 and 2.0 mm, respectively. Electrofusion of the first polar body and the enucleated oocyte is induced by applying 20 V/cm AC for 30 seconds, 3000 V/cm DC for 10 microseconds, and 20 V/cm AC for 90 seconds, consecutively.

The membrane-intact first polar body may be directly introduced into an enucleated oocyte by microinjection. First polar bodies prepared as described above, wherein the plasma membrane of the polar body has been broken by sucking it into the injection pipette during harvesting of the polar body, may also be introduced into the enucleated oocyte by microinjection. In the event of a broken plasma membrane, at least a portion of the first polar body containing all the chromosomes is injected into an enucleated oocyte.

In a preferred method of microinjection of a first polar body (or at least a portion of the polar body including all the chromosomes) into a recipient enucleated oocyte, the piezo electrically-driven micropipette is used. For injection into an oocyte, a single polar body (or the portion thereof) is aspirated deeply into an injection pipette having a short, flat tip with an inner diameter of about 10 μm housed in the piezo electrically-actuated unit according to the instructions of the vendor. Throughout the injection of the polar body (or the portion thereof), the enucleated oocyte is anchored by a conventional holding pipette. The tip of the injection pipette is then brought into intimate contact with the zona pellucida of the oocyte and several piezo pulses (using controller setting scales of intensity 1–5, speed 4–6) are applied to advance the pipette while maintaining a light negative pressure within. When the tip of the pipette has passed through the zona pellucida, the resultant zona plug is expelled into the perivitelline space and the polar body (or the portion thereof) is pushed forward until it is near the tip of the pipette. The pipette tip is then apposed to the plasma membrane and advanced mechanically (toward the opposite face of the oocyte) and the holding pipette almost reaches the opposite side of the cortex of the oocyte. The oocyte plasma membrane is now deeply invaginated around the tip of the injection needle. Upon application of one to two piezo pulses (intensity 1–2, speed 1), the oolernma is punctured at the pipette tip, as indicated by a rapid relaxation of the oolemma, which may be clearly visible. The polar body (or portion thereof) is then expelled into the ooplasm with a minimum amount (about 6 pL) of accompanying medium. The pipette is then gently withdrawn, leaving the newly introduced polar body/polar body chromosomes within the cytoplasm of the oocyte.

Alternative microinjection variants, in which a conventional injection pipette is employed, may be used to inject first polar bodies or at least the portion thereof including all the chromosomes. An example of a suitable microinjection method for insertion of a polar body or the chromosomes thereof into an enucleated oocyte is one that employs a conventional pipette for injecting a sperm head into hamster oocyte, is described in Yanagida, K., Yanagimachi, R., Perreault, S. D. and R. G. Kleinfeld, *Biology of Reproduction* 44, 440–447 (1991), the disclosure of which pertaining to such method is hereby incorporated by reference.

Oocytes injected with first polar bodies may be incubated in a suitable culture medium, such as CZB, under mineral oil, for up to 2 hours at 37.5° C. under 5% $CO_2$ in air before fertilization by a spermatozoon or a spermatozoon nucleus (head).

Fertilization of Enucleated Oocytes

Spermatozoa suitable for fertilizing the oocytes by the method of the invention may be fresh, frozen/thawed, or reconstituted freeze-dried spermatozoa (disclosed in our copending U.S. patent application, Ser. No. 09/177,391, previously incorporated by reference). Fertilization of the oocytes may be achieved with live spermatozoa by in vitro methods known to those skilled in the art, wherein the live spermatozoa pass through the oocyte's vestments by themselves, then fuses with the oocyte. Alternatively, fertilization may be achieved by direct insertion of the entire spermatozoon or by insertion of the sperm head (nucleus) or demembranated sperm head into the oocyte, by microinjection, such as that described above for microinjection of the first polar bodies.

Demembranated sperm heads are detergent-extracted heads that lack all membranes, including the plasma membrane and inner and outer acrosomal membranes, but retain the nucleus and perinuclear material. For example, sperm heads may be demembranated by treatment with Triton X-100. Triton X-100 is a well known non-ionic surfactant that is widely used for removal of membrane components under non-denaturing conditions. In the mouse, sperm heads demembranated by using Triton X-100 have been shown to be capable of activating oocytes, leading to normal embryonic development. A method for demembranating sperm heads is disclosed in our copending U.S. patent application Ser. No. 09/177,391.

In a preferred embodiment, the piezo electrically-driven micropipette is used. for microinjection. For example, a single spermatozoon is aspirated, tail first, into an injection pipette having a short, flat tip with an inner diameter of about 10 μm housed in the piezo electrically-actuated unit according to the instructions of the vendor. The entire spermatozoon may be injected. Alternatively, the sperm head (nucleus) only may be injected. In this case, the sperm head and tail are separated by applying a single or a few Piezo pulses to the neck region. The head is then drawn deeply into the pipette prior to injection. Throughout the injection of the spermatozoon or sperm head, the oocyte is anchored by a conventional holding pipette. The tip of the injection pipette containing a selected spermatozoon or sperm head is brought into intimate contact with the zona pellucida of an oocyte and several piezo pulses (using controller isetting scales of intensity 1–5, speed 4–6) are applied to advance the pipette while maintaining a light negative pressure within. When the tip of the pipette has passed through the zona pellucida, the resultant zona plug is expelled into the perivitelline space and the sperm head is pushed forward until it is near the tip of the pipette. The pipette tip is then apposed to the plasma membrane and advanced (toward the opposite face of the oocyte) and the holding pipette almost reaches the opposite side of the cortex of the oocyte. The oocyte plasma membrane is now deeply invaginated around the tip of the injection needle. Upon application of one to two piezo pulses (intensity 1–2, speed 1), the oolemma is punctured at the pipette tip, as indicated by a rapid relaxation of the oolemma, which may be clearly visible. The spermatozoon or sperm head is then expelled into the ooplasm with a minimum amount (about 6 pL) of accompanying medium. The pipette is then gently withdrawn, leaving the newly introduced spermatozoon or sperm head within the cytoplasm of the oocyte.

Alternative microinjection variants, in which a conventional injection pipette is employed, may also be used to inject spermatozoa or sperm heads, as described above for insertion of the first polar body.

Microinjection of the spermatozoon/sperm head/ demembranated sperm head offers several advantages. First, spermatozoon/sperm head delivery by microinjection is applicable to a wide variety of spermatozoa types, irrespective of size, morphology, and the like. Second, microinjection allows carefully controlled co-injection (with the donor spermatozoon/sperm head) of additional agents into the oocyte at the time of injection. These are exemplified below. Third, in the embodiment of the invention wherein insertion of the spermatozoon/sperm head is by piezo electrically-actuated microinjection, rapid and efficient processing of samples is afforded, thereby reducing trauma to sperm and oocytes undergoing manipulation. The oocytes of some species (e.g., mouse) are not amenable to microinjection using conventional needles, whereas piezo electrically-actuated microinjection affords a high success rate.

Introduction of the Second Polar Body Into Fertilized Enucleated Oocytes

As described above, pronucleus stage fertilized oocytes may be obtained from animals that have ovulated spontaneously or have been induced to ovulate by injection with gonadotrophins, as above, and mated around the time of ovulation. Fertilized oocytes may be obtained surgically from oviducts several hours after ovulation and freed from cumulus cells by treatment with a dispersing enzyme, such as hyaluronidase. Fertilized oocytes may also be obtained by known in vitro fertilization methods employing live spermatozoa, or by insertion of whole spermatozoa or sperm heads into the oocyte.

Removal of the resident chromosomes of the recipient fertilized oocyte must be done prior to or after fertilization has occurred. For example, Met II chromosomes may be removed prior to in vitro fertilization or the female pronucleus removed after fertilization, by a method such as that described above for removal of the Met II chromosomes from the enucleated oocytes. The female pronucleus is selected on the basis of its proximal location to the second polar body and, in some species (e.g., the mouse), its small size relative to the other pronucleus (male pronucleus).

The second polar body may be introduced into the pervitelline space of the fertilized oocyte from which the resident chromosomes or female pronucleus has been removed, and fused with the oocyte by membrane fusion methods described above, including electrofusion. Alternatively, the second polar body may be inserted directly into the fertilized oocyte by microinjection, preferably piezo electrically-actuated microinjection, by methods such as those described above for introduction of the first polar body or portion thereof containing the chromosomes.

Development of Embryos to Produce Viable Fetuses and Offspring

Following female pronucleus formation by the chromosomes of the first or second polar bodies, and fusion of the male and female pronuclei, the resulting embryo may be allowed to develop by culture to the 2–8 cell stage or morula/blastocyst stage, at which time the embryo may be transferred into the oviduct or uterus of a foster mother.

Alternatively, the embryo may be split and the cells clonally expanded, for the purpose of improving yield. Alternatively or additionally, it may be possible for increased yields of viable embryos to be achieved by means of the present invention by clonal expansion of donors and/or if use is made of the process of serial (nuclear) transfer, whereby nuclear constituents from resulting embryos may be transferred back into an enucleated oocyte, according to methods known to those skilled in the art, to rate a new embryo. In a further embodiment of the invention, the pronuclear embryo is cultured in vivo following direct transfer into a suitable recipient.

Modulation of Cell Division or Embryonic Development

In one embodiment of the invention, insertion of the first or second polar body chromosomes and/or fertilization of an oocyte permits the introduction, prior to, during, or after the combining of the chromosomes with the recipient oocyte, or prior to, during, or after fertilization, of one or more agents with the potential to alter the developmental outcome of the embryo. For example, polar body chromosomes may be co-injected with antibodies directed against proteins with hypothetical regulatory roles with the potential to influence the outcome of the method of the invention. Such molecules may include, but are not limited to, proteins involved in vesicle transport (e.g., synaptotagmins), those which may mediate chromatinooplasm communication (e.g., DNA damage cell cycle check-point molecules such as chk1), those with a putative role in oocyte signaling (e.g., STAT3) or those which modify DNA (e.g., DNA methyltransferases). Members of these classes of molecules may also be the indirect targets of modulatory pharmacological agents introduced by microinjection and which have roles analogous to those of antibodies. Both antibodies and pharmacological agents work by binding to their respective target molecules. Where the target has an inhibitory effect on developmental outcome, this binding reduces target function, and where the target has a positive effect on developmental outcome, the binding promotes that function. Alternatively, modulation of functions important in the cloning process may be achieved directly by the injection of proteins (e.g., those in the classes above) rather than agents which bind to them.

In a further embodiment of the invention, exogenous ribonucleic acid (RNA) or deoxyribonucleic acid (DNA) may be introduced into the oocyte by microinjection prior to or following polar body chromosome introduction and/or fertilization. For example, injection of recombinant DNA harboring the necessary cis-active signals may result in the transcription of sequences present on the recombinant DNA by resident or co-injected transcription factors, and subsequent expression of encoded proteins with an antagonistic effect on development inhibitory factors, or with a positive effect on embryo development. Moreover, the transcript may possess antisense activity against mRNAs encoding development inhibitory proteins. Alternatively, antisense regulation may be achieved by injecting exogenous nucleic acids (or their derivatives) that are able to exert an inhibitory effect by interacting directly with their nucleic acid target(s) without prior transcription within the oocyte.

Recombinant DNA (linear or otherwise) introduced by the method of the invention may comprise a functional replicon containing one or more expressed, functional gene under the control of a promoter exhibiting anything from a narrow to a broad developmental expression profile. For example, the promoter might direct immediate, but brief expression where that promoter is active only in the early zygote. Introduced DNA may either be lost at some point during embryonic development, or integrate at one or more genomic loci, to be stably replicated throughout the life of the resulting transgenic individual. In one embodiment, DNA constructs encoding putative "anti-aging" proteins, such as telerase or superoxide dismutase, may be introduced into the oocyte by microinjection. Alternatively, such proteins may be injected directly.

EXAMPLES

The following examples illustrate the methods of the invention. In particular, the examples illustrate the development of normal mice from enucleated mouse oocytes that have been reconstituted with the chromosomes of the first polar body of the same or a donor oocyte, fertilized with at least the head (nucleus) of a spermatozoon, and allowed to develop into embryos that are transplanted into host recipient females and become live, fertile offspring.

The examples described herein are not intended to be limiting, as other examples of embodiments of the invention would readily be recognized by those skilled in the art.

Media and Reagents

Harvested oocytes and fertilized eggs were cultured in a bicarbonate-buffered CZB medium (Chatot, et al., 1989. *J. Reprod. Fert.* 86:, 679–688), under mineral oil, at 37.5° C. under 5% $CO_2$ in air. CZB medium comprises 81.6 mM NaCl, 4.8 mM KCl, 1.7 mM $CaCl_2$, 1.2 mM $MgSO_4$, 1.8 mM $KH_2PO_4$, 25.1 mM $NaHCO_3$, 0.1 mM $Na_2EDTA$, 31 mM Na.lactate, 0.3 mM Na.pyruvate, 7 U/ml penicillin G, 5 U/ml streptomycin sulfate, and 4 mg/ml bovine serum albumin. The medium for oocyte collection from oviducts, subsequent treatments and micromanipulation was a modified CZB containing 20 mM Hepes, a reduced amount of $NaHCO_3$ (5 mM) and bovine serum albumin (BSA) at 3 mg/ml. This medium is herein termed Hepes-CZB. All oocyte manipulations were carried out in Hepes-buffered CZB (Hepes-CZB) under mineral oil at room temperature (23°–25° C.) in air. The pH of both media was approximately 7.4. Although buffered CZB media were used in these examples, other proper media may be substituted, as is known to those skilled in the art.

Animals

Animals used in these examples were maintained in accordance with the guidelines of the Laboratory Animal Service at the University of Hawaii and those prepared by the Committee on Care and Use of Laboratory Animals of the Institute of Laboratory Resources National Research Council (DHEW publication no. [NIH] 80-23, revised in 1985). The protocol of animal handling and treatment was reviewed and approved by the Animal Care and Use Committee at the University of Hawaii.

B6D2F1 female mice (black), 8–10 weeks old, were used as the donors of oocytes and polar bodies. C3H females (agouti; 10 weeks old) and CD1 females (albino; 10–15 weeks old) were also used as polar body donors. Spermatozoa were collected from caudae epididymides of B6D2F1 males, 10 weeks old. Foster mothers were CD1 females.

Micromanipulation

Conventional oocyte-holding and injecting pipettes were used. The inner diameter of the injection pipette at its tip was approximately 10 $\mu$m for oocyte enucleation and was 7–8 $\mu$m for suction and injection of the first polar body.

Example 1

Preparation of Recipient Oocytes

B6D2F1 female mice were superovulated by consecutive injections of 5 international units (IU) equine chorionic gonadotrophin (eCG) and 5 IU of human chorionic gonadotrophin (hCG) 48 hours apart. About 14 hours after hCG injection, oocyte-cumulus complexes were released from oviducts into Hepes-CZB. Cumulus cells were dispersed by a 10 minute treatment with 0.1% bovine testicular hyaluronidase (300USP units/mg; ICN Pharmaceuticals, Costa Mesa, Calif.) in Hepes-CZB. Cumulus-free oocytes were kept in CZB at 37.5° C. under 5% $CO_2$ in air for less than one hour before further treatments.

Example 2

Enucleation of Recipient Oocytes

Enucleation of Met II oocytes was performed in Hepes-CZB containing 5 $\mu$g/mL cytochalasin B. The oocytes were kept in this medium for about 10 minutes at 25° C. before enucleation. Enucleation of the oocytes was achieved by aspiration with a piezo electric-driven micropipette using the Piezo Micromanipulator Model MB-U by Prime Tech Ltd. (Tsukuba, Ibaraki-ken, Japan). This unit uses the piezo electric effect to advance the pipette holder a very short distance (approximately 0.5 $\mu$m) at a time at very high speed. The intensity and speed of the pulse were regulated by the controller.

Groups of B6D2F1 oocytes (usually 10–15), prepared as above, were transferred into a droplet of Hepes-CZB. An oocyte, held by a holding pipette, was rotated until a small, translucent ooplasmic spot, the location of the metaphase II chromosomes, was detected. After the zona pellucida was drilled with the enucleation pipette (about 10 $\mu$m inner diameter) by application of a few piezo pulses, its tip was advanced until it reached the translucent spot in the ooplasm. The translucent ooplasm (with metaphase II chromosomes) was sucked into the pipette without breaking the plasma membrane and was gently pulled away from the oocyte until a stretched cytoplasmic bridge was pinched off. As assessed by fixing and staining of the oocytes, or Hoechst 33342 staining, the efficiency of enucleation was 100%.

Example 3

Preparation of First Polar Bodies

Oviductal oocytes were collected from B6D2F1, CD-1, and C3H females, as described above, between 13 and 27 hours after hCG injection. The viability of polar bodies was assessed using a commericlaly available cell viability test kit (Live/dead FertiLight, Molecular Probes, Inc., Eugene, Oreg.) that differentiates between plasma membrane-intact ("live") and damaged ("dead") cells according to the fluorescence staining pattern under a UV microscope. The chromosomes in live polar bodies with intact plasma membranes fluoresced green, whereas those in dead polar bodies fluoresced bright orange-red.

Example 4

Transfer of First Polar Body Chromosomes Into Enucleated Oocytes and Subsequent Sperm Injection The technique for transfer and injection was that used for injection of spermatid nuclei into oocytes, described herein above. An oocyte with a live first polar body was selected, and its zona pellucida was drilled with a piezo electrically-actuated injection pipette. The plasma membrane of the polar body was broken by sucking it into the pipette. The entire contents of the broken polar body were immediately injected into an enucleated oocyte.

In a separate series of experiments, the entire contents of a dead polar body were injected.

Oocytes injected with polar bodies were incubated in CZB for 2 hours at 37.5° C. under 5% $CO_2$ in air before a second injection of a spermatozoon. Immediately prior to sperm injection, individual spermatozoa were decaptitated by applying a few piezo pulses to the neck region. A single spermatozoon head was injected into each oocyte. This injection was performed at room temperature (23°–25° C.).

Example 5

Oocyte Examination and Embryo Transfer

Some oocytes were examined between 10 minutes and 2 hours after injection to determine how polar body chromosomes behaved within the oocyte's cytoplasm. Other oocytes were examined 5 to 6 hours later for incidence of normal fertilization. Those with one second polar body and two pronuclei were considered normally fertilized and were cultured in CZB medium overnight. Regular 2-cell stage embryos were then transferred into oviducts of recipient females that had been mated with vasectomized males during the previous night.

In one series of experiments, C3H mice were used as polar body donors, and all the recipient oocytes and spermatozoa were from B6D2F1 mice. C3H mice are homologous in four hair color genes, A (agouti), B (brown), C (albino), and D (dilute), i. e., the mice are either A/A, B/B, C/C or D/D. On the contrary, B6D2F1 mice are either a/a, B/b, C/C or D/d. If enucleation of B6D2F1 oocytes had failed, and they were fertilized by B6D2F1 spermatozoa, the coats of all offspring would have been black (i.e., the offspring would have been a/a, B/+, C/C or D/+), brown (i. e., a/a, b/b, C/C or D/+), or gray (i. e., a/a, +/+, C/C or d/d), but not agouti or white in color. If only C3H polar body chromosomes and B6D2F1 sperm chromosomes had participated in the development of enucleated oocytes, all offspring would be expected to have agouti coats (i.e., A/A, B/+, C/C or D/+).

Example 6

Recovery of Live Offspring

On the 19th day post coitum (dpc), recipient females without apparent signs of pregnancy were killed and their uteri were examined for the presence of fetuses. Caesarian section was necessary because recipient females carrying 2 fetuses or less are unable to deliver by themselves. Live fetuses, if any, were raised by lactating CD1 (albino) foster females. Other females were allowed to deliver and raise their offspring.

RESULTS

Figure 2:
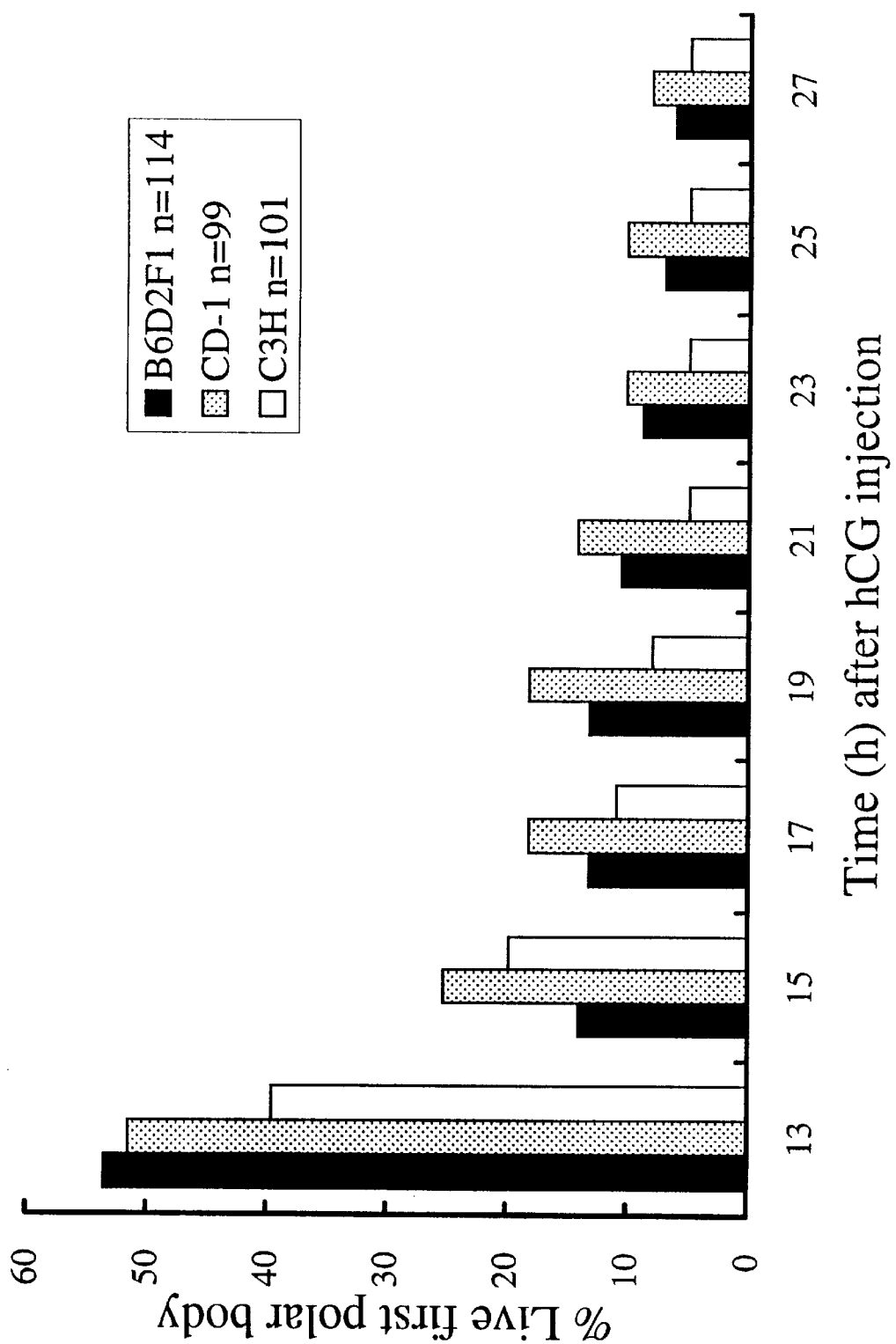
FIG. 2 is a graphical representation of the percentages of live polar bodies obtained at various times after ovulation in a hybrid mouse strain (B6D2F1) and two inbred strains of the mouse (CD-1 and C3H). n=number of oocytes employed.

The proportion of viable first polar bodies at various times after hCG injection is illustrated in FIG. 2. As ovulation in the mouse occurs between 10 and 14 hours after hCG injection, most first polar bodies seem to have degenerated before or soon after ovulation. Nevertheless, 5%–15% of polar bodies were viable for many hours after ovulation.

Figure 3:
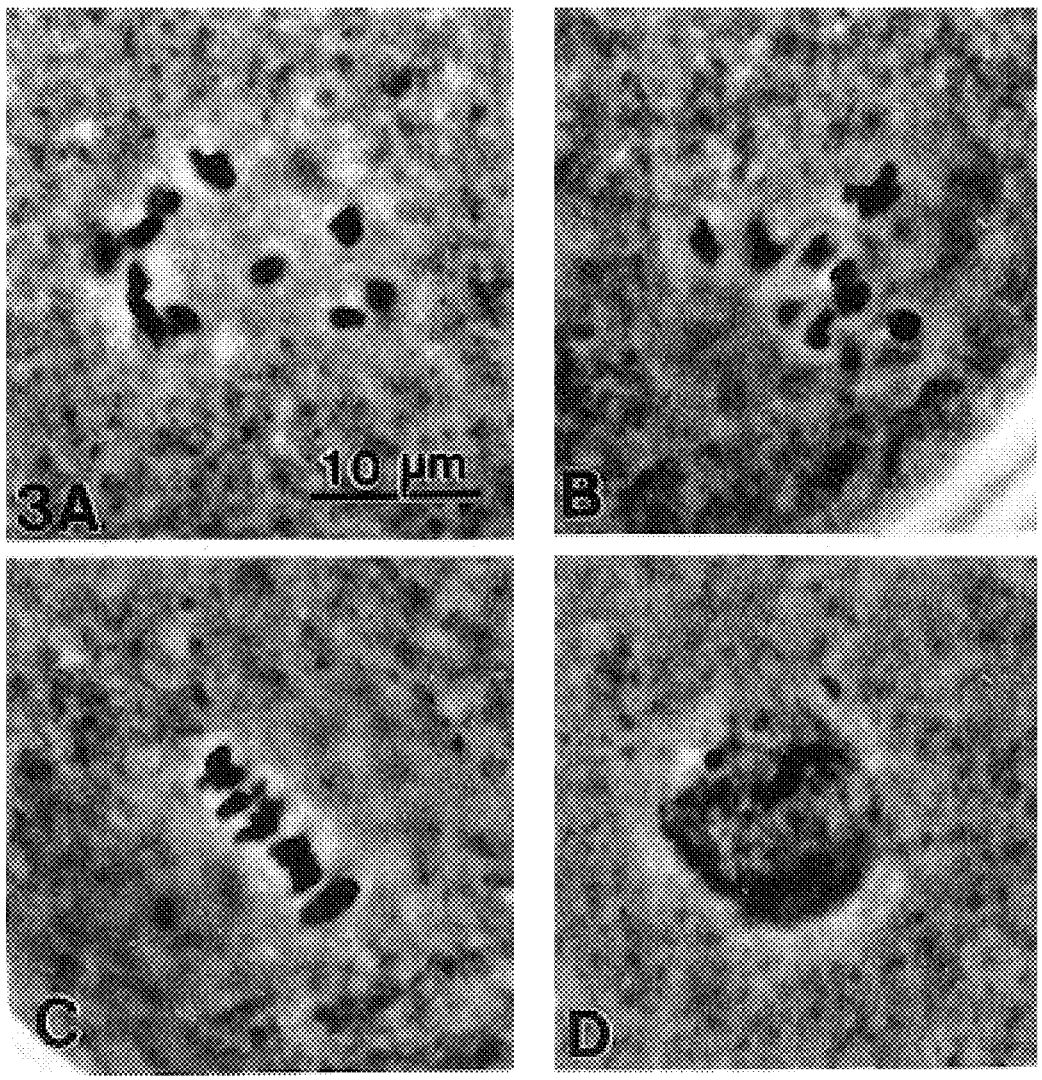
FIGS. 3A–3D illustrate photomicrographs of the transformation of the first polar body chromosomes into metaphase II chromosomes within enucleated oocytes. (A) Shortly after injection into the oocyte, the chromosomes are scattered. (B) and (C) The chromosomes gradually aggregate and are arranged on the metaphase plate by 2 hours after injection. (D) Chromosomes in the dead polar body, injected into the oocyte, cannot be organized to form a chromosome-spindle complex.

When a live first polar body was injected into an enucleated oocyte, the polar body chromosomes aggregated gradually (see FIG. 3, A and B). By 2 hours after injection, the chromosomes were arranged on the metaphase plate of the second meiotic division (see FIG. 3C). Chromosomes in dead polar bodies did not transform into typical metaphase chromosomes (FIG. 3D).

Figure 4:
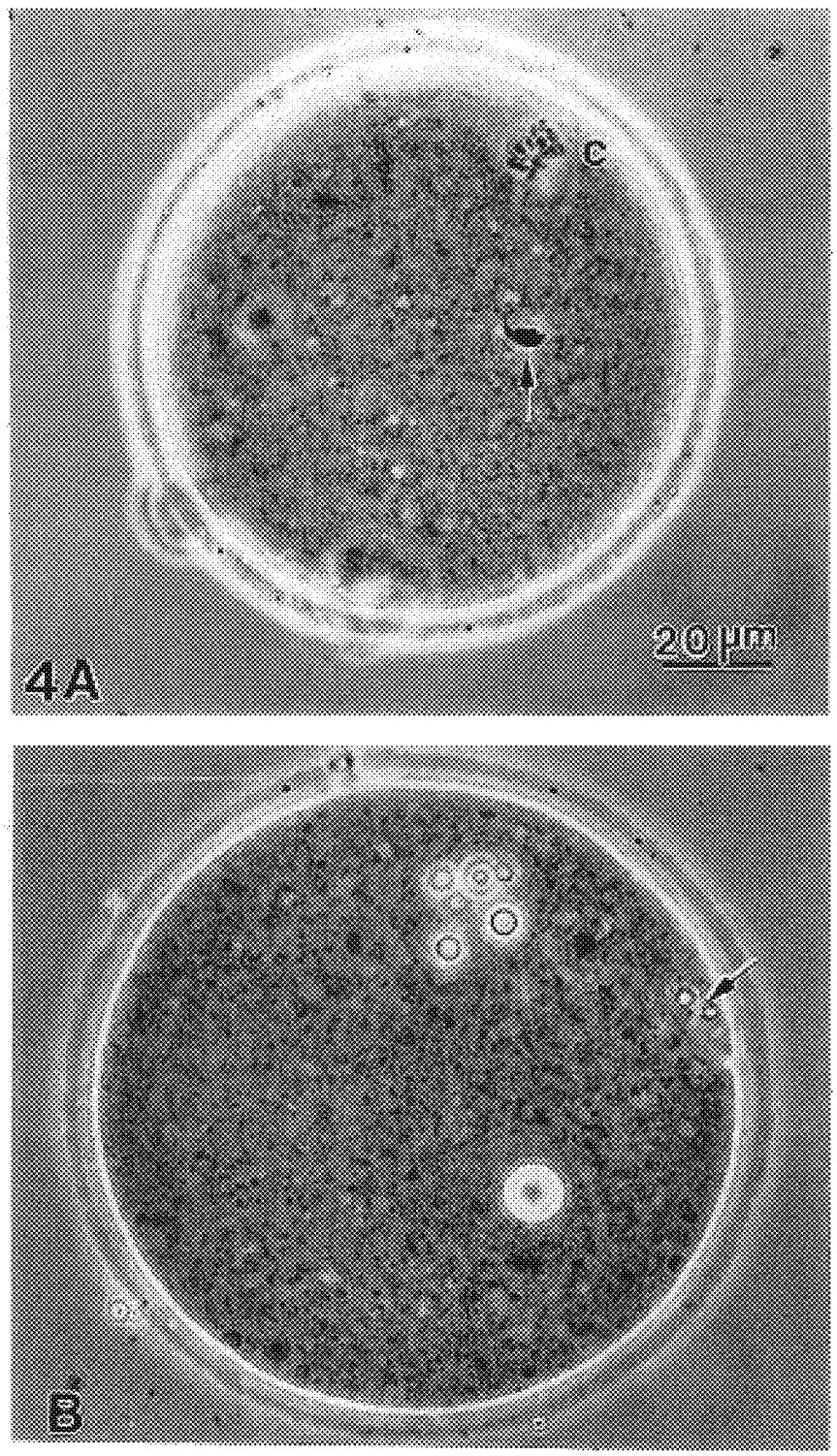
FIGS. 4A–4B illustrate photomicrographs of the fertilization of an oocyte with the first polar body chromosomes instead of its own chromosomes. (A) This oocyte was enucleated, and then first polar body chromosomes were transferred, and then the oocyte was injected with a spermatozoon head. This photograph was taken about 10 minutes after sperm injection. An arrow indicates a sperm head within the oocyte. (B) An oocyte (egg) at 5 hours after sperm injection, with two pronuclei and one (second) polar body (arrow).

As illustrated in Table 1, about half (i.e., 92) of a total of 171 enucleated oocytes injected with live first polar bodies survived. After a single spermatozoon head injection (see e.g., FIG. 4A), 79 of the surviving 92 oocytes were fertilized normally (see e.g., FIG. 4B) regardless of the postovulatory age of the polar bodies. Transfer of 74 two-cell embryos to 11 foster mothers resulted in the birth of 27 normal offspring. Of these, 3 were born by caesarean section of two females. Others were delivered naturally.

All 27 offspring were raised, and mating among them was carried out. Each of the 15 females of the offspring became pregnant and had litters of the normal size of 8–12 pups.

In the above experiments, it was observed that the rate of oocyte survival after polar body injection was not very high, perhaps because of the large size of the injection pipette. It is believed that the oocyte survival rate could possibly be increase through technical improvements. Moreover, the mouse oocyte (about 75 $\mu$m in diameter) has a relatively large first polar body (about 10 $\mu$m in diameter). Microsurgical procedures, such as those reported here, will probably prove easier than polar bodies are smaller relative to the size of the oocyte, such as in animals (e.g. cattle) and in humans.

Using both the first and second polar body for production of fertile offspring, the genetic information in one oocyte can be transmitted to four offspring. Because recipient oocytes are enucleated prior to transfer of polar body chromosomes, all offspring will have no genetic influence from donors of the recipient oocytes other than from the maternal (oocyte) mitochondria. Because each recipient oocyte receives a different spermatozoon, i.e., the four oocytes receive different maternal and paternal genes, this mode of reproduction does not represent cloning. In an extreme situation in which only a few females of a species remain, the use of polar bodies in this way mat help to increase the genetic diversity of offspring, provided that recipient oocytes of closely related species are readily available.

While the invention has been described herein with reference to the preferred embodiments, it is to be understood that it is not intended to limit the invention to the specific forms disclosed. On the contrary, it is intended to cover all of the manifold modifications and alternative forms falling within the spirit and scope of the invention.

TABLE 1

Development of Mouse Enucleated Oocytes Injected With First Polar Chromosomes (Pb1c) and Spermatozoa

| | | Number of Enucleated Oocytes | | | | |
| --- | --- | --- | --- | --- | --- | --- |
| Source of Pb1c | Time after hCG Injection When Pb1c Were Collected | Total | Surviving After Pb1c Injection (%) | Normally Fertilized After Sperm Injection | No. of 2-Cell Embryos Transferred (No. of Foster Mothers) | No. of Live Offspring (%) |
| B6D2F1 | 15 hours | 61 | 35 (57) | 30 | 28 (6) | 16 (57) |
|  | 20 hours | 85 | 41 (48) | 39 | 36 (3) | 18 (50) |
| C3H | 15 hours | 25 | 16 (64) | 10 | 10 (2) | 3 (30) |

We claim:

1. A method for obtaining an embryo having chromosomes derived from a first polar body, comprising the steps of:

collecting a live first polar body from a first oocyte;

introducing at least a portion of the first polar body that includes all the chromosomes into an enucleated recipient oocyte to form a chromosomally reconstituted recipient oocyte;

fertilizing the reconstituted recipient oocyte; and allowing the fertilized reconstituted recipient oocyte to develop into an embryo.

2. The method of claim 1, further comprising the steps of transferring the embryo to a surrogate mother and allowing the embryo to develop into a live offspring.

3. The method of claim 1, wherein the first polar body chromosomes are introduced into the enucleated recipient oocyte by microinjection.

4. The method of claim 3, wherein the microinjection is piezo-electrically actuated microinjection.

5. The method of claim 1, wherein the first polar body chromosomes are introduced into the enucleated recipient oocyte by fusion of the polar body with the oocyte.

6. The method of claim 5, wherein the fusion is by fusion-promoting chemicals or by electricity or by a fusogenic virus.

7. The method of claim 1, wherein the step of fertilizing the reconstituted recipient oocyte comprises exposing the oocyte to a live spermatozoon.

8. The method of claim 1, wherein the step of fertilizing the reconstituted recipient oocyte comprises inserting a whole spermatozoon or a spermatozoon head or a demembranated spermatozoon head into the oocyte.

9. The method of claim 8, wherein the insertion of the whole spermatozoon or the spermatozoon head or the demembranated spermatozoon head is by piezo electrically-actuated microinjection.

10. A method for producing multiple embryos using the chromosomes of a single oocyte, comprising the steps of:

collecting a live first polar body from a first oocyte;

fertilizing the first oocyte after removal of the first polar body;

allowing the first fertilized oocyte to develop into a first embryo;

introducing at least a portion of the first polar body that contains the chromosomes into an enucleated second oocyte to form a chromosomally reconstituted second oocyte;

fertilizing the reconstituted second oocyte; and allowing the fertilized reconstituted second oocyte to develop into a second embryo.

11. The method of claim 10, further comprising the steps of transferring at least one of the first and second embryos to a surrogate mother and allowing the at least one embryo to develop into a live offspring.

12. The method of claim 10, further comprising the steps of:

obtaining a live second polar body from the fertilized first oocyte;

obtaining a fertilized enucleated third oocyte;

introducing at least a portion of the live second polar body that contains the chromosomes into the fertilized enucleated third oocyte; and allowing the fertilized third oocyte to develop into a third embryo.

13. The method of claim 12, further comprising the steps of transferring the third embryo to a surrogate mother and allowing the third embryo to develop into a live offspring.

14. The method of claim 12, further comprising the steps of:

obtaining a live second polar body from the fertilized second oocyte;

obtaining a fertilized enucleated fourth oocyte;

introducing at least a portion of the second polar body from the fertilized second oocyte into the fertilized enucleated fourth oocyte, wherein the introduced portion of the second polar body contains the chromosomes; and allowing the fertilized fourth oocyte to develop into a fourth embryo.

15. The method of claim 14, further comprising the steps of transferring the fourth embryo to a surrogate mother and allowing the fourth embryo to develop into a live offspring.

* * * * *